(12) United States Patent
Shikama

(10) Patent No.: US 11,467,725 B2
(45) Date of Patent: Oct. 11, 2022

(54) OPERATION TARGET SWITCHING APPARATUS, OPERATION TARGET SWITCHING METHOD, AND OPERATION TARGET SWITCHING PROGRAM

(71) Applicant: Konica Minolta Inc., Tokyo (JP)

(72) Inventor: Jo Shikama, Machida (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 17/087,060

(22) Filed: Nov. 2, 2020

(65) Prior Publication Data
US 2021/0191587 A1 Jun. 24, 2021

(30) Foreign Application Priority Data
Dec. 20, 2019 (JP) .............................. JP2019-230690

(51) Int. Cl.
*G06F 3/0488* (2022.01)
*G06F 3/04842* (2022.01)
*A61B 8/00* (2006.01)
*G06F 3/041* (2006.01)

(52) U.S. Cl.
CPC ............ *G06F 3/0488* (2013.01); *A61B 8/465* (2013.01); *A61B 8/469* (2013.01); *G06F 3/0416* (2013.01); *G06F 3/04842* (2013.01)

(58) Field of Classification Search
CPC .. G06F 3/0488; G06F 3/0416; G06F 3/04842; A61B 8/465; A61B 8/469
See application file for complete search history.

(56) References Cited

U.S. PATENT DOCUMENTS

| | | | | |
|---|---|---|---|---|
| 2002/0191029 | A1* | 12/2002 | Gillespie | G06F 3/04817 715/810 |
| 2010/0179427 | A1* | 7/2010 | Yamamoto | A61B 8/469 600/443 |
| 2020/0187908 | A1* | 6/2020 | Schmied | G06F 3/04886 |

FOREIGN PATENT DOCUMENTS

| | | | | |
|---|---|---|---|---|
| EP | 3561656 A1 * | 10/2019 | | A61B 5/743 |
| JP | 2016-220830 A | 12/2016 | | |

* cited by examiner

*Primary Examiner* — Sanjiv D. Patel
(74) *Attorney, Agent, or Firm* — Rankin, Hill & Clark LLP

(57) ABSTRACT

An operation target switching apparatus includes: a display part that displays an operation target that a user can select and operate; an operation input part that receives an input of a touch operation on an operation part not dedicated to an instruction for switching selection of the operation target; and a hardware processor that switches the selection of the operation target, in accordance with a mode of the touch operation.

18 Claims, 5 Drawing Sheets

OPERATION TARGET SWITCHING APPARATUS, OPERATION TARGET SWITCHING METHOD, AND OPERATION TARGET SWITCHING PROGRAM

The entire disclosure of Japanese patent Application No. 2019-230690, filed on Dec. 20, 2019, is incorporated herein by reference in its entirety.

BACKGROUND

Technological Field

The present invention relates to an operation target switching apparatus, an operation target switching method, and an operation target switching program.

Description of the Related Art

There have been ultrasound diagnostic imaging apparatuses that are known for transmitting and receiving ultrasound waves with an ultrasound probe to and from a subject such as a living organism, generating ultrasound image data on the basis of signals obtained from received ultrasound waves, and displaying an ultrasound image based on the ultrasound image data on an image display apparatus. Ultrasound diagnostic imaging by an ultrasound diagnostic imaging apparatus can obtain the state of the heart beat or the movement of a fetus or the like in real time through a simple operation of bringing an ultrasound probe into contact with the surface of the subject, and is non-invasive and highly safe. Thus, the ultrasound diagnostic imaging can be repeatedly performed.

In an ultrasound diagnostic imaging apparatus, an operation target is operated through a touch operation performed on a touch screen by the user, for example, while the operation target (such as a measurement cursor or a region of interest) that can be selected and operated by the user (the operator) is displayed. In a case where the operation target is a region of interest, for example, the region of interest can be moved to a desired position by the user's drag operation.

Further, in an ultrasound diagnostic imaging apparatus, selection of an operation target is switched by a user's touch operation while the operation target is displayed (see JP 2016-220830 A, for example).

JP 2016-220830 A discloses setting of a first region displaying operation buttons on which the operator can perform a touch operation to issue an instruction to switch the selection of an operation target, and a second region on which the operator can perform a slide operation.

By the technology disclosed in JP 2016-220830 A, however, when switching the selection of an operation target, the user needs to move his/her hand to the position of an operation button (a software key) formed at the lower left corner of the screen, resulting in an increase in the operation time and a decrease in operability. In a general ultrasound diagnostic imaging apparatus, a dedicated hardware key for issuing an instruction to switch selection of an operation target is normally formed at a predetermined position.

SUMMARY

An object of the present invention is to provide an operation target switching apparatus, an operation target switching method, and an operation target switching program that are capable of increasing the operability in switching selection of an operation target.

To achieve the abovementioned object, according to an aspect of the present invention, an operation target switching apparatus reflecting one aspect of the present invention comprises: a display part that displays an operation target that a user can select and operate; an operation input part that receives an input of a touch operation on an operation part not dedicated to an instruction for switching selection of the operation target; and a hardware processor that switches the selection of the operation target, in accordance with a mode of the touch operation.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
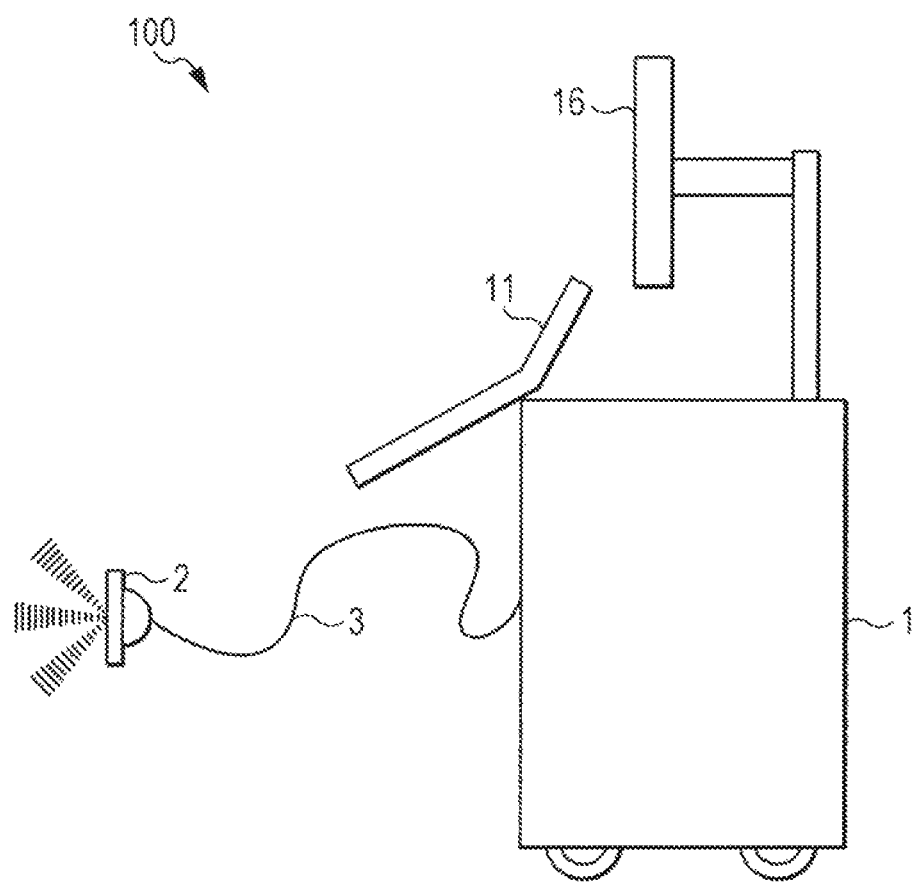
FIG. 1 is an external view of an ultrasound diagnostic imaging apparatus.

Hereinafter, an ultrasound diagnostic imaging apparatus 100 according to one or more embodiments of the present invention will be described with reference to the drawings. However, the scope of the invention is not limited to the disclosed embodiments. FIG. 1 is an external view of the ultrasound diagnostic imaging apparatus 100.

As shown in FIG. 1, the ultrasound diagnostic imaging apparatus 100 includes an ultrasound diagnostic imaging apparatus main body 1 and an ultrasound probe 2. The ultrasound diagnostic imaging apparatus 100 functions as an "operation target switching apparatus" according to an embodiment of the present invention.

The ultrasound probe 2 transmits ultrasound waves (transmission ultrasound waves) to the inside of a subject such as a living organism (not shown), and receives reflected waves of the ultrasound waves reflected in the subject (reflected ultrasound waves: echo).

The ultrasound diagnostic imaging apparatus main body 1 is connected to the ultrasound probe 2 via a cable 3, and transmits a drive signal that is an electrical signal to the ultrasound probe 2, to cause the ultrasound probe 2 to transmit transmission ultrasonic waves to the subject.

The ultrasound diagnostic imaging apparatus main body 1 also images the internal state of the subject as an ultrasound image, on the basis of a reception signal that is an electrical signal generated by the ultrasound probe 2 in accordance with the reflected ultrasound waves the ultrasound probe 2 has received from the inside of the subject. Further, the ultrasound diagnostic imaging apparatus main body 1 includes an operation input part 11 and a display part 16 that will be described later.

The ultrasound probe 2 includes transducers 2*a* (see FIG. 2) that are formed with piezoelectric elements. The transducers 2*a* are arranged in a one-dimensional array in the azimuth direction (the scanning direction), for example. In this embodiment, an ultrasound probe 2 including 192 transducers 2a is used, for example.

The transducers 2a may be arranged in a two-dimensional array. Also, the number of transducers 2a can be set as appropriate. In this embodiment, a linear electronic scanning probe is used as the ultrasound probe 2 to perform ultrasound scanning by a linear scanning method. However, either a sector scanning method or a convex scanning method can also be adopted. Communication between the ultrasound diagnostic imaging apparatus main body 1 and the ultrasound probe 2 may be conducted by wireless communication such as Ultra Wide Band (UWB), instead of wire communication via the cable 3.

Figure 2:
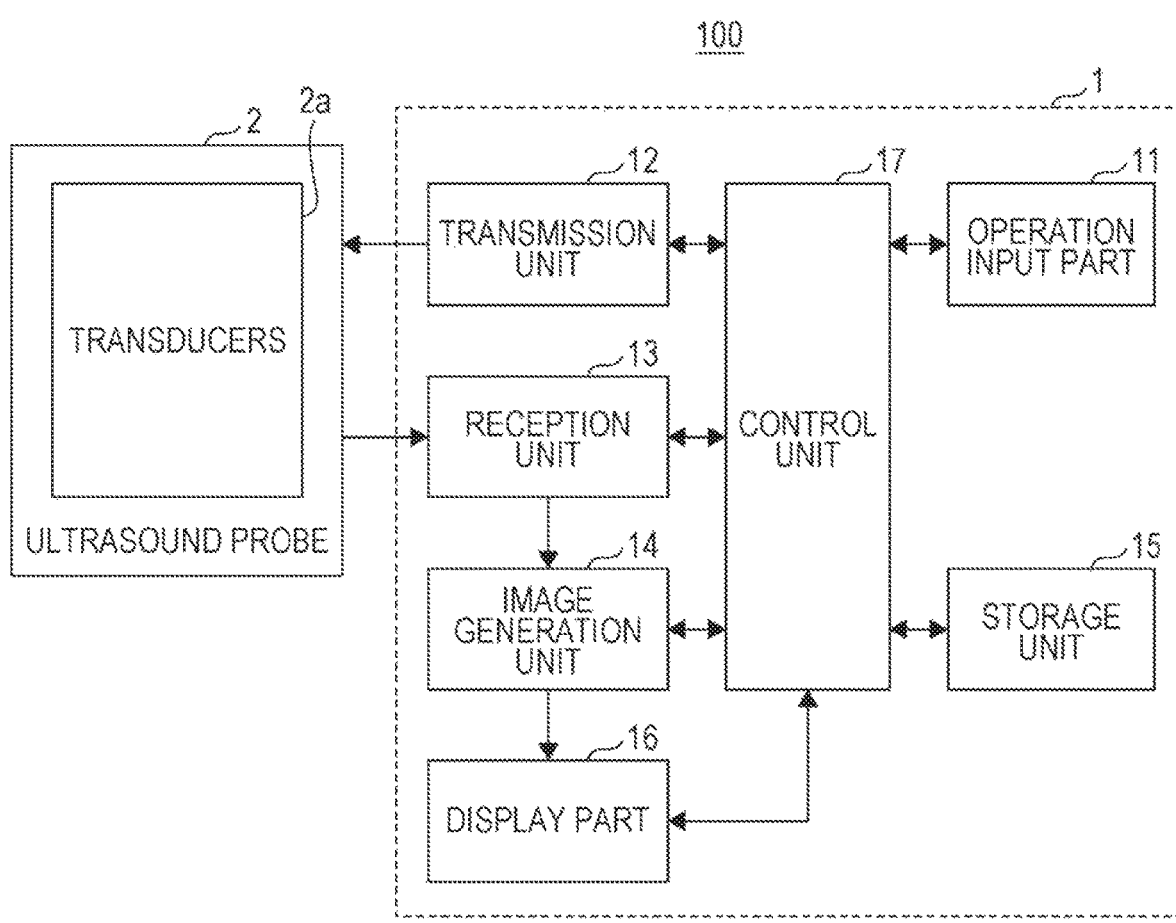
FIG. 2 is a block diagram showing the functional configuration of the ultrasound diagnostic imaging apparatus.

Next, the functional configuration of the ultrasound diagnostic imaging apparatus 100 is described, with reference to FIG. 2. FIG. 2 is a block diagram showing the functional configuration of the ultrasound diagnostic imaging apparatus 100.

As shown in FIG. 2, the ultrasound diagnostic imaging apparatus main body 1 includes an operation input part 11, a transmission unit 12, a reception unit 13, an image generation unit 14, a storage unit 15, a display part 16, and a control unit 17, for example. The control unit 17 functions as a "selection switching part" according to an embodiment of the present invention.

The operation input part 11 includes various switches, buttons, a track pad, a trackball, a mouse, a keyboard, and a touch screen that is formed integrally on the display screen of the display part 16 and senses a touch operation performed on the display screen (the touch screen functions as an "operation part not dedicated to an instruction to switch selection of an operation target" according to an embodiment of the present invention). The operation input part 11 receives inputs of a diagnosis start instructing command, data such as personal information about the subject, and various parameters for displaying an ultrasound image on the display part 16, for example. The operation input part 11 then outputs an operation signal corresponding to the input operation, to the control unit 17.

The transmission unit 12 is a circuit that supplies a drive signal that is an electrical signal to the ultrasound probe 2 via the cable 3 and causes the ultrasound probe 2 to generate transmission ultrasound waves, under the control of the control unit 17.

Further, the transmission unit 12 includes a clock generation circuit, a delay circuit, and a pulse generation circuit, for example. The clock generation circuit is a circuit that generates a clock signal that determines the transmission timing and the transmission frequency of the drive signal. The delay circuit sets a delay time for each individual path associated with each corresponding transducer 2a, delays transmission of the drive signal by the set delay time, and focuses a transmission beam formed by transmission ultrasound waves (transmission beam forming), for example. The pulse generation circuit is a circuit for generating a pulse signal as the drive signal at a preset voltage and preset time intervals.

Under the control of the control unit 17, the transmission unit 12 designed as described above sequentially switches the transducers 2a to which the drive signal is to be supplied while shifting the transducers 2a by a predetermined number every time ultrasound waves are transmitted/received. The transmission unit 12 then supplies the drive signal to the transducers 2a selected as the output designations. By doing so, the transmission unit 12 performs scanning.

The reception unit 13 is a circuit that receives a reception signal that is an electrical signal from the ultrasound probe 2 via the cable 3, under the control of the control unit 17. The reception unit 13 includes an amplifier, an A/D converter circuit, and a phasing adder circuit, for example.

The amplifier is a circuit for amplifying a reception signal with a preset amplification factor for each individual path associated with each corresponding transducer 2a. The A/D converter circuit is a circuit for performing analog-digital conversion (A/D conversion) on the amplified reception signal. The phasing adder circuit is a circuit for generating sound ray data by assigning a delay time to the A/D-converted reception signal for each individual path associated with each corresponding transducer 2a to adjust the time phase, and adding up the results (phasing addition). That is, the phasing adder circuit performs reception beam forming on the reception signal of each transducer 2a, to generate sound ray data.

Under the control of the control unit 17, the image generation unit 14 performs an envelope detection process, logarithmic compression, and the like on the sound ray data from the reception unit 13, and performs dynamic range and gain adjustment, to achieve luminance conversion. By doing so, the image generation unit 14 generates brightness (B) mode image data (hereinafter referred to as ultrasound image data) as tomographic image data. That is, the ultrasound image data indicates the intensity of the reception signal in terms of luminance.

Further, the image generation unit 14 includes an image memory unit (not shown) that is formed with a semiconductor memory such as a dynamic random access memory (DRAM). The image generation unit 14 stores the generated ultrasound image data into the image memory unit on a frame-by-frame basis.

The image generation unit 14 also performs image processing such as an image filtering process and a time smoothing process on the ultrasound image data read from the image memory unit, to scan and convert the ultrasound image data into a display image pattern for display on the display part 16.

The storage unit 15 is a storage unit, such as a flash memory, a hard disk drive (HDD), or a solid state drive (SSD), on which writing and reading of information can be performed.

The display part 16 is a display device such as a liquid crystal display (LCD), a cathode-ray tube (CRT) display, an organic electronic luminescence (EL) display, an inorganic EL display, or a plasma display. The display part 16 displays an ultrasound image corresponding to the ultrasound image data generated by the image generation unit 14 on the display screen, under the control of the control unit 17.

The control unit 17 includes a central processing unit (CPU), a read only memory (ROM), and a random access memory (RAM), for example. The control unit 17 reads various processing programs such as a system program stored in the ROM, loads the programs into the RAM, and, according to the loaded programs, centrally controls operations of the respective parts of the ultrasound diagnostic imaging apparatus main body 1.

The ROM is formed with a non-volatile memory such as a semiconductor, and stores a system program compatible with the ultrasound diagnostic imaging apparatus 100, various processing programs executable on the system program, various kinds of data such as a gamma table, and the like. These programs are stored in the form of computer-readable program codes, and the CPU sequentially performs operations according to the program codes. The RAM forms a work area that temporarily stores various programs executed by the CPU and data related to these programs. In this embodiment, the ROM of the control unit 17 stores an "operation target switching program".

The ultrasound diagnostic imaging apparatus 100 is provided with a measurement mode for carrying out various kinds of measurement on the target portion (a structure or a lesion in the living organism, for example) in the subject, on the basis of a generated ultrasound image. In the measurement mode, it is possible to measure the distance between two points, the length of a traced shape, the diameter of a circle or an ellipse, circumference and area, angle, time, volume, and the like, for example As shown in FIG. 3, in a case where an examination screen 20 including an ultrasound image is displayed on the display part 16, for example, the user of the ultrasound diagnostic imaging apparatus 100 (the examiner, for example) presses a measurement button (not shown), to switch to the measurement mode.

Figure 3:
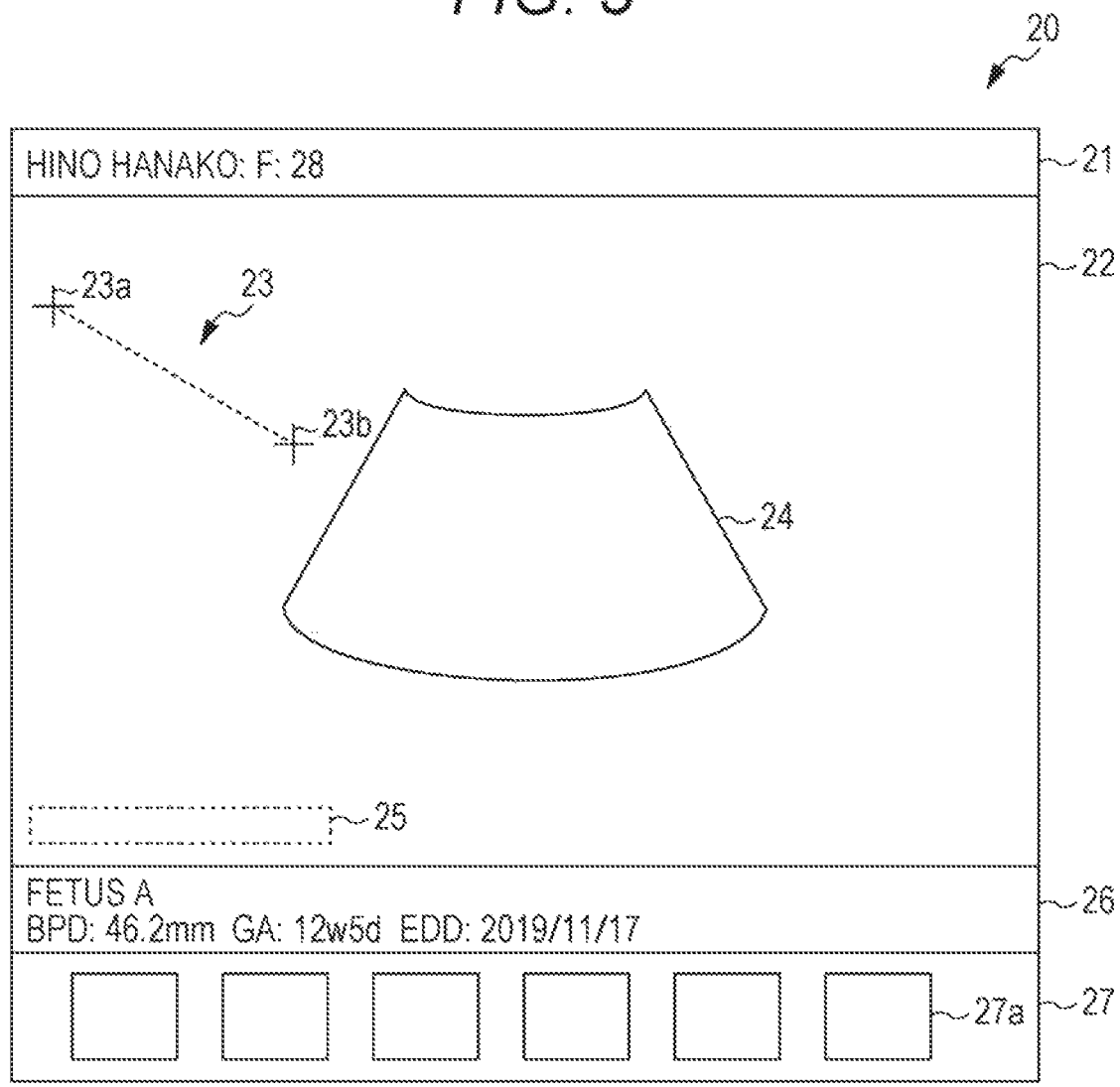
FIG. 3 is a diagram showing an example display of an examination screen.

The example shown in FIG. 3 illustrates switching to a measurement mode for measuring the size of a biparietal diameter (BPD), with the measurement site being the fetus in the body of a pregnant woman.

A display region 21 of the examination screen 20 displays the name of the pregnant woman as the subject (HINO Hanako, for example), sex (F, for example), age (28, for example), and the like.

A display region 22 of the examination screen 20 displays an ultrasound image, and operation targets the user can select and operate (a measurement cursor 23 and a region of interest 24 in the example shown in FIG. 3). A measurement process is then performed in accordance with an operation performed on the measurement cursor 23 by the user. Here, the measurement cursor 23 is a mark for indicating a current position such as a point or an axis required for measurement of a target portion in the subject, and includes a start point cursor 23*a*, an end point cursor 23*b*, and the like.

Meanwhile, the region of interest 24 is a region indicating a specific site that is a target of diagnosis, examination, or the like in the displayed ultrasound image. The control unit 17 changes the position of the region of interest 24 or changes the size of the region of interest 24 in the display region 22, in accordance with a user's instruction input through the operation input part 11.

It is possible to display an ultrasound image including a measurement site, by pressing a freeze button of the operation input part 11 when the measurement site is shown in an ultrasound image acquired through pressing of the ultrasound probe 2 against the subject, for example.

In accordance with the user's instruction input through the operation input part 1, the control unit 17 moves and determines the positions of the start point cursor 23*a* and the end point cursor 23*b*, and measures the size of the measurement site in the ultrasound image on the basis of the determined positions. After moving and determining the position of the start point cursor 23*a* in accordance with the user's instruction, the control unit 17 causes the end point cursor 23*b* to be displayed at a certain distance from the start point cursor 23*a* at the determined position, in the direction designated by the user through the operation input part 11. The control unit 17 further moves and determines the end point cursor 23*b* in accordance with the user's instruction. Every time the control unit 17 measures the size of a measurement site, the control unit 17 stores the size as a measurement value into the storage unit 15. Note that the positions of the start point cursor 23*a* and the end point cursor 23*b* are determined by a confirming operation such as pressing a "Set" button of the operation input part 11.

A display region 26 of the examination screen 20 displays the BPD (46.2 mm, for example) of the fetus (a fetus A, for example) existing in the body of a pregnant woman, the gestational age (GA: 12 weeks (w) and five days (d), for example) estimated from the measured BPD, the estimated date of delivery (EDD: Nov. 17, 2019, for example) estimated from the GA, and the like. The gestational age corresponds to the number of days of pregnancy as of the date of the examination.

A display region 27 of the examination screen 20 displays operation buttons 27*a* (software keys) for performing various kinds of settings in the ultrasound diagnostic imaging apparatus 100.

In this embodiment, to increase the operability in switching selection of an operation target (the measurement cursor 23 or the region of interest 24), the operation input part 11 receives an input of a touch operation on the display region 22 displaying an ultrasound image in the examination screen 20 (corresponding to a "display screen" according to an embodiment of the present invention), via a touch screen that senses a touch operation performed on the display screen of the display part 16. The control unit 17 then switches the selection of the operation target, in accordance with the mode of the touch operation input to the operation input part 11.

For example, in a case where the size of the region of interest 24 is selected as the operation target, when the touch operation input to the operation input part 11 is a slide touch operation (a tracing operation), the control unit 17 switches selection of the operation target from the size of the region of interest 24 to the position of the region of interest 24, which is a related function. Further, when the touch operation input to the operation input part 11 is a multi-touch operation (a simultaneous touch operation at a plurality of points), the control unit 17 switches selection of the operation target from the size of the region of interest 24 to the position of the measurement cursor 23 (the start point cursor 23*a* and the end point cursor 23*b*), which is not a related function. That is, the control unit 17 changes the operation target as a switch destination, in accordance with the mode of the touch operation (specifically, the type of the touch operation). The touch operation that is input to the operation input part 11 to switch selection of the operation target is only required to be an operation including at least one type of a plurality of types of touch operations. For example, the touch operation may be an operation other than a slide touch operation and a multi-touch operation (such as a successive touch operation such as a double tap or a triple tap, or a long-press operation), or may be a touch operation formed with at least two touch operations among a slide touch operation, a multi-touch operation, and a touch operation that is neither a slide touch operation nor a multi-touch operation.

As shown in FIG. 3, the display region 22 of the examination screen 20 includes a display region 25 that displays various kinds of images relating to switching of selection of the operation target. FIGS. 4A to 4E are diagrams showing example displays of various kinds of images relating to switching selection of an operation target. Note that the display region 25 may be formed outside the display region 22.

Figure 4A:
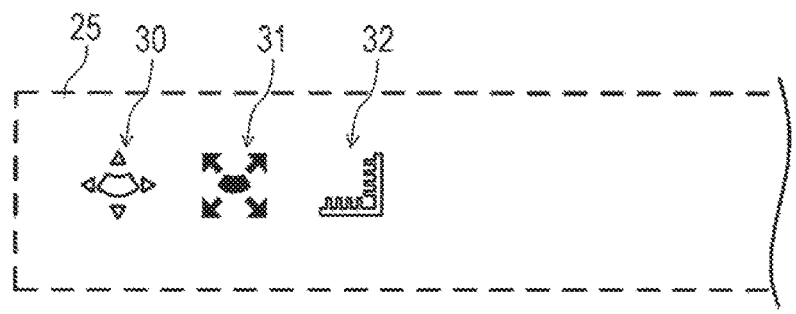
FIGS. 4A to 4E are diagrams showing example displays of various kinds of images relating to switching selection of an operation target.

As shown in FIG. 4A, in the display region 25, an icon image 30 indicating the "position of the region of interest 24" as an operation target, an icon image 31 indicating the "size of the region of interest 24" as an operation target, and an icon image 32 indicating the "position of the measurement cursor 23" as an operation target are displayed side by side. Further, the icon image 31 indicating the currently selected operation target is displayed in a different display mode from that for the icon images 30 and 32 indicating the operation targets not currently selected. Specifically, the icon image 31 is displayed with a color (blue, for example), while the icon images 30 and 32 are displayed without any color. By viewing the display region 25 shown in FIG. 4A, the user can easily understand that the currently selected operation target is the "size of the region of interest 24".

Figure 4B:
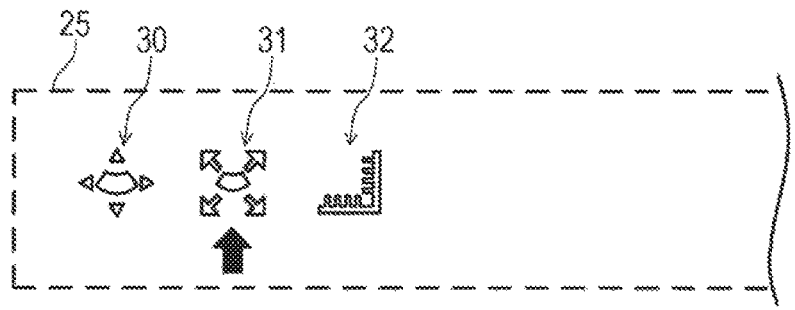

As shown in FIG. 4B, an upward-pointing arrow image may be displayed below the icon image 31 indicating the currently selected operation target, so that the icon image 31 indicating the currently selected operation target is displayed in a different display mode from that for the icon images 30 and 32 indicating the operation targets not currently selected. Further, instead of the icon images 30, 31, and 32 each indicating the currently selected operation target or an unselected operation target, character string images indicating the respective operation targets may be displayed. Alternatively, while the icon image 31 is displayed in a large size, the icon images 30 and 32 may be displayed in a small size.

Figure 4C:
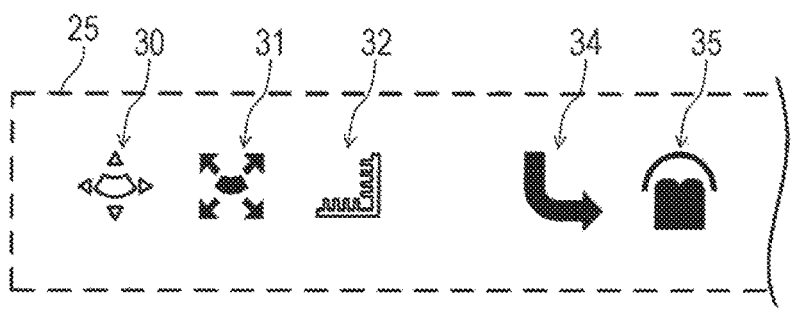

As shown in FIG. 4C, in the display region 25, the icon image 30 indicating the "position of the region of interest 24" as an operation target, the icon image 31 indicating the "size of the region of interest 24" as an operation target, and the icon image 32 indicating the "position of the measurement cursor 23" as an operation target are displayed side by side. In the display region 25, an operation image 34 indicating the mode of the touch operation necessary for switching the currently selected operation target (the size of the region of interest 24) to the "position of the region of interest 24" is also displayed in conjunction with the icon image 30. In the display region 25, an operation image 35 indicating the mode of the touch operation necessary for switching the operation target (the size of the region of interest 24) to the "position of the measurement cursor 23" is further displayed in conjunction with the icon image 32. The operation image 34 is an icon image indicating a slide touch operation as a touch operation mode in which the touching finger slides downward and then to the right. The operation image 35 is an icon image indicating a multi-touch operation (a two-point simultaneous touch operation) as a touch operation mode. By viewing the display region 25 shown in FIG. 4C, the user can easily understand the mode of the touch operation necessary for switching the currently selected operation target, for each operation target as a switch destination. Alternatively, character string images indicating the respective operation targets (the "position of the region of interest 24" and the "position of the measurement cursor 23") as switch destinations may be displayed in conjunction with the respective operation images 34 and 35. Further, character string images indicating the functions (switching of operation targets) of the operation images 34 and 35 may be displayed in conjunction with the respective operation images 34 and 35.

Figure 4D:
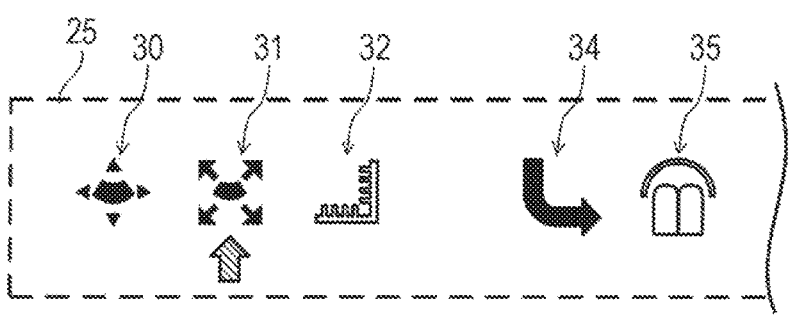

As shown in FIG. 4D, in the display region 25, the icon image 30 indicating the "position of the region of interest 24" as an operation target, the icon image 31 indicating the "size of the region of interest 24" as an operation target, and the icon image 32 indicating the "position of the measurement cursor 23" as an operation target are displayed side by side. Here, the icon image 31 indicating the currently selected operation target (the size of the region of interest 24) is colored, and an upward-pointing arrow image is displayed below the icon image 31. In the display region 25, the operation image 34 indicating the mode of the touch operation necessary for switching the currently selected operation target (the size of the region of interest 24) to the "position of the region of interest 24", and the operation image 35 indicating the mode of the touch operation necessary for switching the operation target (the size of the region of interest 24) to the position of the "measurement cursor 23" are also displayed.

In the example shown in FIG. 4D, the operation images 34 and 35 are displayed in a different display mode for each operation target as a switch destination. Specifically, the operation image 34 is associated with the colored icon image 30 indicating an operation target (the position of the region of interest 24) as a switch destination, and is displayed in the same color as the icon image 30. On the other hand, the operation image 35 is associated with the uncolored icon image 32 indicating an operation target (the position of the measurement cursor 23) as a switch destination, and is displayed in an uncolored manner like the icon image 32. By viewing the display region 25 shown in FIG. 4D, the user can understand the correspondence relationship between the operation targets as the switch destinations and the modes of the touch operations necessary for switching to the operation targets as the switch destinations, more easily than with the display region 25 shown in FIG. 4C.

Figure 4E:
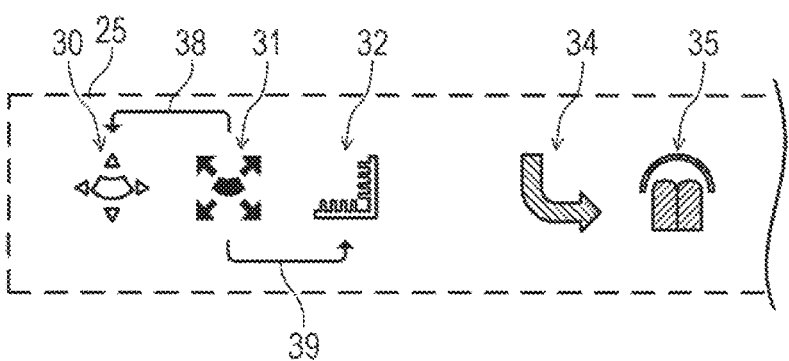

In the example shown in FIG. 4E, the operation images 34 and 35 are displayed in a different display mode for each operation target as a switch destination. Specifically, the colored operation image 34 is associated with the icon image 30 indicating an operation target (the position of the region of interest 24) as a switch destination, and is displayed. The operation image 35 that is in a different color from the operation image 34 is associated with the icon image 32 indicating an operation target (the position of the measurement cursor 23) as a switch destination, and is displayed. Further, above the icon images 30 and 31, an arrow image 38 that is in the same color as the operation image 34, and indicates switching of selection from the size of the region of interest 24 (the icon image 31) to the position of the region of interest 24 (the icon image 30) is displayed. Below the icon images 31 and 32, an arrow image 39 that is in the same color as the operation image 35, and indicates switching from the size of the region of interest 24 (the icon image 31) to the position of the measurement cursor 23 (the icon image 32) is also displayed. By viewing the display region 25 shown in FIG. 4E, the user can understand the correspondence relationship between the operation targets as the switch destinations and the modes of the touch operations necessary for switching to the operation targets as the switch destinations, more easily than with the display region 25 shown in FIG. 4C.

Figure 5:
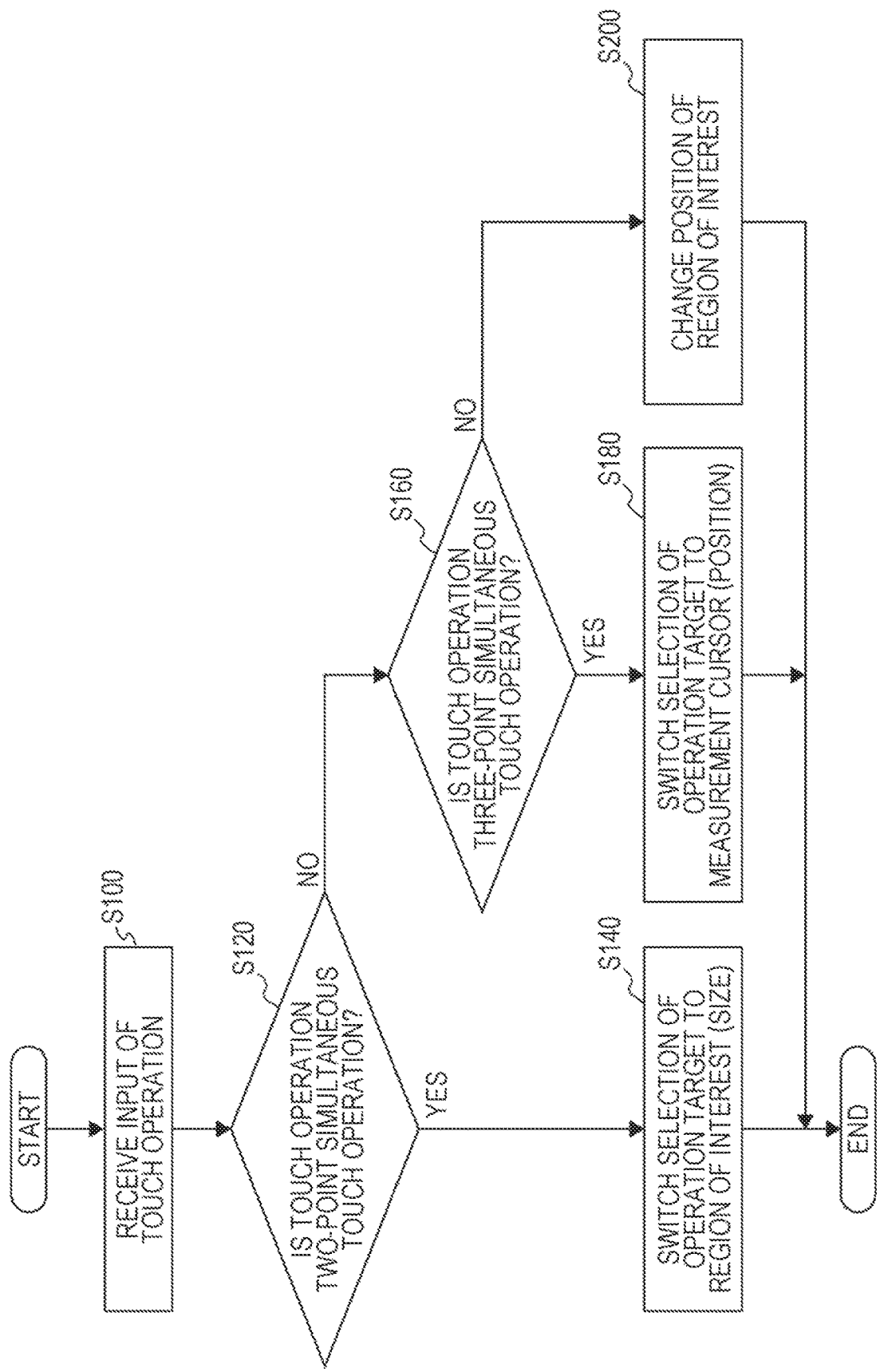
FIG. 5 is a flowchart showing an example operation of the ultrasound diagnostic imaging apparatus.

FIG. 5 shows a flowchart showing an example operation to switch selection of an operation target in the ultrasound diagnostic imaging apparatus 100. The process in step S100 starts when an ultrasound image is displayed in the display region 22 of the examination screen 20 in the measurement mode. At this stage, the measurement cursor 23 and the region of interest 24 are displayed together with the ultrasound image in the display region 22 of the examination screen 20, and the "position of the region of interest 24" is selected as the operation target the user can operate.

First, the operation input part 11 receives an input of a touch operation on the display region 22 displaying the ultrasound image in the examination screen 20, via a touch screen that senses a touch operation performed on the display screen of the display part 16 (step S100).

The control unit 17 then determines whether the touch operation input to the operation input part 11 is a multi-touch operation (a two-point simultaneous touch operation) (step S120). If the result of the determination shows that the input touch operation is a two-point simultaneous touch operation (step S120, YES), the control unit 17 switches selection of the operation target from the "position of the region of interest 24" to the "size of the region of interest 24" (step S140). As the process in step S140 is completed, the ultrasound diagnostic imaging apparatus 100 ends the process shown in FIG. 5.

If the input touch operation is not a two-point simultaneous touch operation (step S120, NO), on the other hand, the control unit 17 determines whether the touch operation input to the operation input part 11 is a multi-touch operation (a three-point simultaneous touch operation) (step S160).

If the result of the determination shows that the input touch operation is a three-point simultaneous touch operation (step S160, YES), the control unit 17 switches selection of the operation target from the "position of the region of interest 24" to the "position of the measurement cursor 23" (step S180). As the process in step S180 is completed, the ultrasound diagnostic imaging apparatus 100 ends the process shown in FIG. 5.

If the result of the determination shows that the input touch operation is not a three-point simultaneous touch operation, but is a slide touch operation, for example (step S160, NO), the control unit 17 does not switch selection of the operation target, but changes the position of the region of interest 24 selected as the operation target, in accordance with the operation mode (such as the operating direction or the amount of operation) of the slide touch operation (step S200). As the process in step S200 is completed, the ultrasound diagnostic imaging apparatus 100 ends the process shown in FIG. 5.

As described above in detail, in this embodiment, the ultrasound diagnostic imaging apparatus 100 (an operation target switching apparatus) includes: the display part 16 that displays operation targets (the measurement cursor 23 and the region of interest 24) the user can select and operate: the operation input part 11 that receives an input of a touch operation performed on a touch screen (the operation part) not dedicated to an instruction to switch selection of an operation target; and the control unit 17 (the selection switching part) that switches the selection of the operation target in accordance with the mode of the touch operation.

According to this embodiment designed as described above, selection of an operation target is switched in accordance with the mode of a touch operation performed on the touch screen not dedicated to an instruction to switch the selection of an operation target. Accordingly, when switching the selection of an operation target, the user does not need to move his/her hand to the position of an operation button (a software key) provided at the lower left corner of the screen as in the technology disclosed in JP 2016-220830 A. That is, the operation time for switching the selection of an operation target can be shortened, and operability can be increased. Further, a software key dedicated to an instruction to switch the selection of an operation target is not necessarily formed at a predetermined position (a region on the examination screen 20, for example). Accordingly, it is possible to prevent a decrease in the visibility of an ultrasound image due to a reduction in the size of the display region 22 in which the ultrasound image is displayed, and prevent a decrease in the operability of the operation buttons 27a due to a reduction in the size of the operation buttons 27a displayed in the display region 27. Thus, an inadvertent operation error can be prevented. Furthermore, it is possible to eliminate the need to form a dedicated hardware key for issuing an instruction to switch the selection of an operation target at a predetermined position.

Further, in this embodiment, the selection of an operation target is switched in accordance with the mode of a touch operation performed on the display region 22 displaying an ultrasound image in the examination screen 20. Accordingly, in a case where the operation buttons 27a (software keys) displayed in the display region 27 are operated by mistake, it is possible to prevent inadvertent operation target switching not desired by the user.

In the example of the embodiment described above, the control unit 17 switches operation targets as switch destinations, in accordance with the type of a touch operation. However, the present invention is not limited to this example. For example, the control unit 17 may change operation targets as switch destinations, in accordance with the position of a touch operation performed on the touch screen.

Further, in the example of the embodiment described above, the touch screen that senses a touch operation performed on the display screen of the display part 16 corresponds to the "operation part" according to an embodiment of the present invention. However, the present invention is not limited to this example. For example, in addition to the touch screen, a track pad that is a pointing device to be used in place of a mouse may have the same functions as those of the "operation part" according to an embodiment of the present invention.

Further, an external track pad, a tablet, or a smartphone (wired and wireless) may have the same functions as those the "operation part" according to an embodiment of the present invention. A display part (functioning as a "second display part" according to an embodiment of the present invention) that is different from the display part 16 may also have the same functions as those of the "operation part" according to an embodiment of the present invention. In short, what corresponds to the "operation part" according to an embodiment of the present invention is only required to be an operation part that is not dedicated to an instruction to switch the selection of an operation target.

Further, in the example of the embodiment described above, the measurement cursor 23 and the region of interest 24 have been described as examples of operation targets the user can select and operate. However, the present invention is not limited to this example. For example, operation targets are not limited to the measurement cursor 23 and the region of interest 24, but may include a body mark. In short, what corresponds to an "operation target" according to an embodiment of the present invention is only required to be an image (or a character string image) that is displayed on the display part and can be operated by the user via the operation part. Here, a body mark is input by the user to indicate information regarding an ultrasound image acquisition site (a scanned site or an observed site) of the subject, and the position of the ultrasound probe in ultrasound image data.

Further, in the example of the embodiment described above, the ultrasound diagnostic imaging apparatus 100 functions as the "operation target switching apparatus" according to an embodiment of the present invention. However, the present invention is not limited to this example. For example, a medical diagnostic imaging apparatus that collects information about the inside of the human body, and generates and displays a medical image showing the states of the structure and the functions inside the human body on the basis of the collected information may function as the "operation target switching apparatus" according to an embodiment of the present invention.

Further, in the embodiment described above, some or all of the functions of the respective functional blocks of the transmission unit 12, the reception unit 13, the image generation unit 14, and the control unit 17 included in the ultrasound diagnostic imaging apparatus 100 can be formed as a hardware circuit such as an integrated circuit. An integrated circuit is an LSI (Large Scale Integration), and an LSI may be called an IC, a system LSI, a super LSI, or an ultra LSI, depending on the degree of integration. Further, the circuit integrating technique is not necessarily that of LSI, but may be realized with a dedicated circuit or a general-purpose processor. Alternatively, a reconfigurable processor that can reconfigure connections and settings of a field programmable gate array (FPGA) and circuit cells inside an LSI may be used. Further, some or all of the functions of each functional block may be executed by software. In this case, this software is stored in one or more storage media such as a ROM, an optical disk, a hard disk, or the like, and this software is executed by an arithmetic processor.

Although embodiments of the present invention have been described and illustrated in detail, the disclosed embodiments are made for purposes of illustration and example only and not limitation. That is, the present invention can be embodied in various forms, without departing from its scope or principal features. The scope of the present invention should be interpreted by terms of the appended claims.

What is claimed is:

1. An operation target switching apparatus comprising:
   a display part that displays operation targets that a user can select and operate, wherein the operation targets include at least two of a region of interest, a measurement cursor and a body mark;
   an operation input part that receives an input of a touch operation on an operation part not dedicated to an instruction for switching a selection of one of the operation targets; and
   a hardware processor that switches the selection from one of the region of interest, the measurement cursor or the body mark as one of the operation targets to another one of the region of interest, the measurement cursor or the body mark as another one of the operation targets, that is different from the one of the region of interest, the measurement cursor or the body mark, in accordance with a mode of the touch operation.

2. The operation target switching apparatus according to claim 1, wherein
   the display part displays an image indicating a currently selected operation target.

3. The operation target switching apparatus according to claim 2, wherein
   the display part displays a character string image indicating the currently selected operation target.

4. The operation target switching apparatus according to claim 1, wherein
   the display part displays an image indicating a currently selected operation target, and a second image indicating an operation target not currently selected.

5. The operation target switching apparatus according to claim 4, wherein
   the display part displays the image indicating the currently selected operation target, and the second image indicating the operation target not currently selected, in different display modes from each other.

6. The operation target switching apparatus according to claim 1, wherein
   the hardware processor changes the operation targets as a switch destination, in accordance with the mode of the touch operation.

7. The operation target switching apparatus according to claim 1, wherein
   the mode of the touch operation is a position of the touch operation on the operation part.

8. The operation target switching apparatus according to claim 1, wherein
   the display part displays an operation image indicating a mode of a touch operation necessary for switching a currently selected operation target.

9. The operation target switching apparatus according to claim 8, wherein
   the display part displays the operation image in a different display mode for each operation target as a switch destination.

10. The operation target switching apparatus according to claim 8, wherein
    the display part displays a character string image indicating an operation target as a switch destination.

11. The operation target switching apparatus according to claim 1, wherein
    the one of the operation targets before the selection is switched by the hardware processor, and the another one of the operation targets after the selection is switched by the hardware processor are related functions.

12. The operation target switching apparatus according to claim 1, wherein
    the one of the operation targets before the selection is switched by the hardware processor, and the another one of the operation targets after the selection is switched by the hardware processor are not related functions.

13. The operation target switching apparatus according to claim 1, wherein
    the operation part is a track pad, or a touch screen that senses a touch operation on a display screen of the display part or a second display part.

14. The operation target switching apparatus according to claim 1, wherein
    the touch operation is an operation including at least one of touch operations of a plurality of types.

15. The operation target switching apparatus according to claim 1, wherein
    the display part displays an ultrasound image of an internal state of a subject,
    the operation part is a touch screen that senses a touch operation on a display screen of the display part, and
    the operation input part receives an input of a touch operation on a region on the display screen, the region displaying the ultrasound image.

16. An operation target switching method comprising:
    displaying operation targets that a user can select and operate, wherein the operation targets include at least two of a region of interest, a measurement cursor and a body mark;
    receiving an input of a touch operation on an operation part not dedicated to an instruction for switching a selection of one of the operation targets; and
    switching the selection from one of the region of interest, the measurement cursor or the body mark as one of the operation targets to another one of the region of interest, the measurement cursor or the body mark as another one of the operation targets, that is different from the one of the region of interest, the measurement cursor or the body mark in accordance with a mode of the touch operation.

17. A non-transitory recording medium storing a computer readable operation target switching program for causing a computer to perform:
    displaying operation targets that a user can select and operate, wherein the operation targets include at least two of a region of interest, a measurement cursor and a body mark;
    receiving an input of a touch operation on an operation part not dedicated to an instruction for switching a selection of one of the operation targets; and
    switching the selection from one of the region of interest, the measurement cursor or the body mark as one of the operation targets to another one of the region of interest, the measurement cursor or the body mark as another one of the operation targets, that is different from the one of the region of interest, the measurement cursor or the body mark, in accordance with a mode of the touch operation.

18. The operation target switching apparatus according to claim 1
    wherein the operation part is a track pad.

\* \* \* \* \*